(12) United States Patent
Hauel et al.

(10) Patent No.: US 8,901,127 B2
(45) Date of Patent: Dec. 2, 2014

(54) PYRIDAZIN DERIVATIVES AS ANTAGONISTS OF THE BRADYKININ B1 RECEPTOR

(75) Inventors: Norbert Hauel, Schemmerhofen (DE); Raimund Kuelzer, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 164 days.

(21) Appl. No.: 13/816,303

(22) PCT Filed: Aug. 19, 2011

(86) PCT No.: PCT/EP2011/064259
§ 371 (c)(1),
(2), (4) Date: Aug. 5, 2013

(87) PCT Pub. No.: WO2012/022794
PCT Pub. Date: Feb. 23, 2012

(65) Prior Publication Data
US 2014/0038977 A1    Feb. 6, 2014

(30) Foreign Application Priority Data
Aug. 20, 2010   (EP) .................................... 10173488

(51) Int. Cl.
  *C07D 405/14*  (2006.01)
(52) U.S. Cl.
  CPC .................................. *C07D 405/14* (2013.01)
  USPC ...................................... 514/252.03; 544/238
(58) Field of Classification Search
  USPC ...................................... 514/252.03; 544/238
  See application file for complete search history.

(56) References Cited

U.S. PATENT DOCUMENTS

2010/0240669 A1    9/2010   Hauel et al.

FOREIGN PATENT DOCUMENTS

| WO | 2005085198 A2 | 9/2005 |
| WO | 2009027450 A1 | 3/2009 |
| WO | 2010097372 A1 | 9/2010 |
| WO | 2011104203 A1 | 9/2011 |

OTHER PUBLICATIONS

International Search Report, Form PCT/ISR/210, and Written Opinion, Form PCT/ISR/237, for Cooresponding Application PCT/EP2011/064259, Date of Mailing Sep. 30, 2011.

*Primary Examiner* — Jeffrey H Murray
*Assistant Examiner* — Oluwafemi Masha
(74) *Attorney, Agent, or Firm* — Michael P. Morris; Anthony P. Bottino

(57) ABSTRACT

The present invention relates to the compounds of general formula I

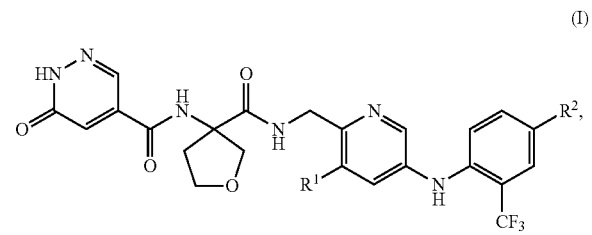

wherein $R^1$ and $R^2$ are defined as described hereinafter, the enantiomers, the diastereomers, the mixtures and the salts thereof, particularly the physiologically acceptable salts thereof with organic or inorganic acids or bases, which have valuable properties, the preparation thereof, the medicaments containing the pharmacologically effective compounds, the preparation thereof and the use thereof.

4 Claims, No Drawings

PYRIDAZIN DERIVATIVES AS ANTAGONISTS OF THE BRADYKININ B1 RECEPTOR

The present invention relates to the compounds of general formula I

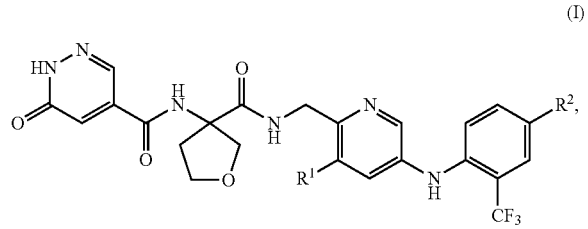

(I)

wherein $R^1$ and $R^2$ are defined as described hereinafter, the enantiomers, the diastereomers, the mixtures and the salts thereof, particularly the physiologically acceptable salts thereof with organic or inorganic acids or bases, which have valuable properties, the preparation thereof, the medicaments containing the pharmacologically effective compounds, the preparation thereof and the use thereof.

BACKGROUND TO THE INVENTION

1. Technical Field

The present invention relates to disubstituted tetrahydrofuranyl compounds and the use thereof as B1-receptor-antagonists, pharmaceutical compositions containing these compounds and method for using them for the prevention or treatment of acute pain, visceral pain, neuropathic pain, inflammatory and pain receptor-mediated pain, tumour pain as well as headaches.

2. State of the Art

Compounds with a B1-antagonistic activity have already been described in the patent applications WO2009/027450 and WO 2010/057899.

One aim of the present invention was to provide new compounds which are particularly suitable as pharmacological active substances in medicaments which can be used for the treatment of diseases that are at least partly mediated by the B1-receptor.

DETAILED DESCRIPTION OF THE INVENTION

In the above general formula I $R^1$ denotes H, Cl or F and $R^2$ denotes Cl or F, the enantiomers, the diastereomers, the mixtures and the salts thereof, particularly the physiologically acceptable salts thereof with organic or inorganic acids or bases.

The following are mentioned as examples of most particularly preferred compounds of the above general formula I:

| No. | Structure |
| --- | --- |
| (1) | 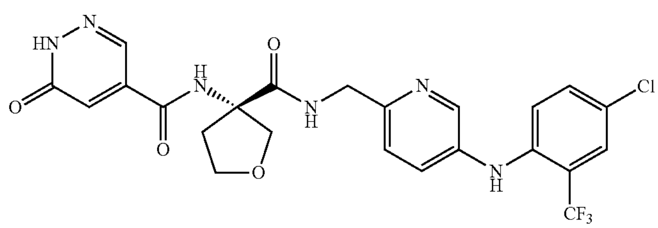 [SMILES: O=C(N[C@@]1(C(=O)NCc2ccc(Nc3ccc(Cl)cc3C(F)(F)F)cn2)CCOC1)c1cn[nH]c(=O)c1] |
| (2) | 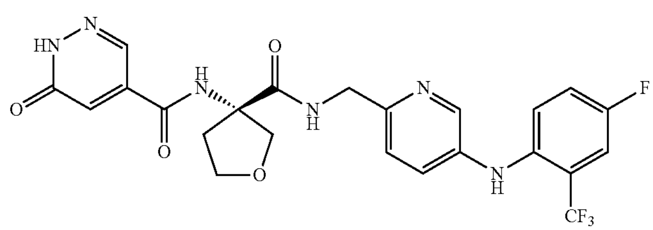 [SMILES: O=C(N[C@@]1(C(=O)NCc2ccc(Nc3ccc(F)cc3C(F)(F)F)cn2)CCOC1)c1cn[nH]c(=O)c1] |
| (3) | 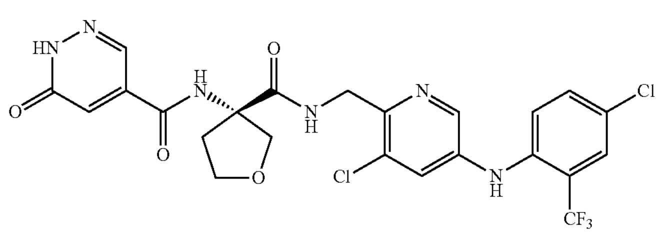 [SMILES: O=C(N[C@@]1(C(=O)NCc2ncc(Nc3ccc(Cl)cc3C(F)(F)F)cc2Cl)CCOC1)c1cn[nH]c(=O)c1] |

| No. | Structure |
|---|---|
| (4) | 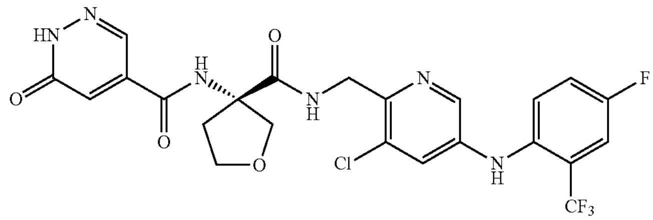 [SMILES: O=C(N[C@@]1(C(=O)NCc2ncc(Nc3ccc(F)cc3C(F)(F)F)cc2Cl)CCOC1)c1cn[nH]c(=O)c1] |
| (5) | 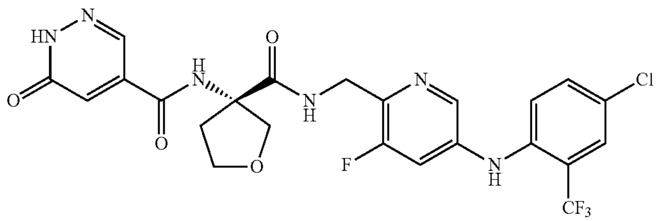 [SMILES: O=C(N[C@@]1(C(=O)NCc2ncc(Nc3ccc(Cl)cc3C(F)(F)F)cc2F)CCOC1)c1cn[nH]c(=O)c1] |
| (6) | | the enantiomers, the diastereomers, the mixtures and the salts thereof, particularly the physiologically acceptable salts thereof with organic or inorganic acids or bases.

TERMS AND DEFINITIONS USED

The subject-matter of this invention includes the compounds according to the invention of general formula I mentioned hereinbefore, including the salts thereof, wherein one or more hydrogen atoms, for example one, two, three, four or five hydrogen atoms, are replaced by deuterium.

Unless stated otherwise, a chemical formula or a name given in the description or in a claim encompasses both all the structurally possible and thermodynamically stable tautomers and also all the stereoisomers, optical isomers, geometric isomers (e.g. enantiomers, diastereomers, E/Z isomers, etc.), racemates and mixtures of different components of the individual enantiomers, mixtures of diastereomers or mixtures of each form mentioned above in which isomers and enantiomers exist.

The invention also encompasses solvates of the compounds of general formula I, for example the hydrates thereof.

The invention also encompasses the salts of the compounds specified in each case, including the physiologically acceptable salts, as well as the solvates, such as hydrates, thereof.

Compounds of general formula I, if they contain suitable basic functions, for example amino groups, may be converted into the physiologically acceptable salts thereof with inorganic or organic acids, particularly for pharmaceutical applications.

By the term "physiologically acceptable salt" is preferably meant, for the purposes of the present invention, salts of the compounds according to the invention which are physiologically acceptable, i.e. particularly for use in humans and/or mammals.

The term "physiologically acceptable" for the purposes of the present invention is used as a reference to those compounds, ingredients, compositions and/or preparations which are suitable for use in contact with human or animal tissue, within the scope of a reasonable medical judgment, without excessive toxicity, irritation, allergic reactions or other problems or complications, and which correspond to a proportionate risk/benefit ratio.

Examples of inorganic acids for this purpose include hydrobromic acid, phosphoric acid, nitric acid, hydrochloric acid or sulphuric acid, while examples of organic acids include formic acid, malic acid, ascorbic acid, benzoic acid, succinic acid, acetic acid, ethylenediaminetetraacetic acid, fumaric acid, glutamic acid, hexane-1-sulphonic acid, carbonic acid, maleic acid, mandelic acid, lactic acid, monomethylsebacic acid, nicotinic acid, oxalic acid, 5-oxoproline, saccharinic acid, sulphonic acids, such as for example methanesulphonic acid, camphorsulphonic acid, ethanesulphonic acid, ethane-1,2-disulphonic acid, benzenesulphonic acid or p-toluenesulphonic acid, tartaric acid or citric acid (cf. "Pharmaceutical salts", Birge, S. M. et al., J. Pharm. Sci., (1977), 66, 1-19).

Moreover, if they contain suitable carboxylic acid functions, the compounds of general formula I may be converted into the physiologically acceptable salts thereof with inorganic or organic bases, particularly for pharmaceutical applications. Examples of inorganic bases for this purpose include alkali or alkaline earth metal hydroxides, for example sodium hydroxide or potassium hydroxide, or carbonate, ammonia, zinc or ammonium hydroxides; examples of organic amines include diethylamine, triethylamine, ethanolamine, diethanolamine, triethanolamine, cyclohexylamine or dicyclohexylamine.

The physiologically acceptable salts according to the present invention may be synthesised starting from the compounds according to the invention which contain a suitable basic or acidic unit, by conventional chemical methods. Generally, salts of this kind may be prepared by reacting the free acid or base group with the required amount of base or acid in water or an organic solvent, such as for example diethyl ether, ethyl acetate, ethanol, isopropanol, acetonitrile or a mixture of these solvents.

The compounds according to the invention may occur as racemates if they have only one chiral element, but they may also be obtained as pure enantiomers, i.e. in (R) or (S) form.

However, the application also includes the individual diastereomeric pairs of antipodes or the mixtures thereof which are present when there is more than one chiral element in the compounds of general formula I, as well as the individual optically active enantiomers of which the above-mentioned racemates are made up.

Compounds with a carbon double bond may be present in both the E and Z forms.

If a compound may be present in different tautomeric forms, the compound shown is not restricted to one tautomeric form, but includes all the tautomeric forms. This also applies particularly in the case of nitrogen-containing heteroaryls:

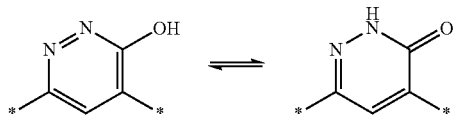 [SMILES: *c1cc(*)c(O)nn1 ; *c1cc(*)c(=O)[nH]n1]

PREPARATION METHODS

According to the invention the compounds of general formula I are obtained by methods known per se, for example by the following methods:

(A) Amide Coupling:

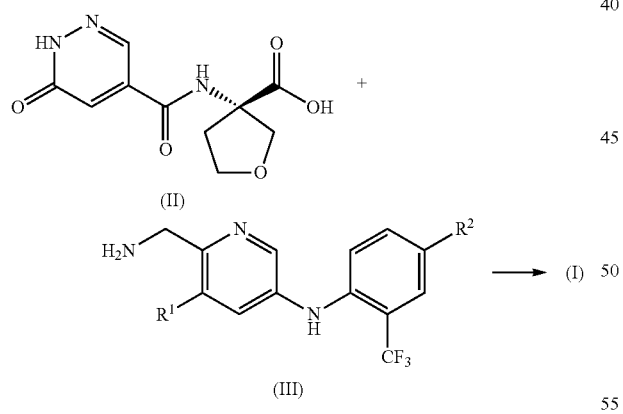

The linking of the carboxylic acid of formula II to amines of general formula III, wherein $R^1$ and $R^2$ are as hereinbefore defined, as illustrated, forming carboxylic acid amides of general formula I wherein $R^1$ and $R^2$ are as hereinbefore defined, may be carried out by conventional methods of amide formation.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran (THF), acetonitrile, dimethyl formamide (DMF), dimethyl acetamide (DMA), N-methylpyrrolidone (NMP) or mixtures thereof. If necessary, an auxiliary base such as for example diisopropylethylamine (DIPEA, Hünig base) is additionally used.

It is also possible to convert the carboxylic acid of formula II into the corresponding carboxylic acid chloride and then react this with amines of general formula III, wherein $R^1$ and $R^2$ are as hereinbefore defined. The synthesis of carboxylic acid chlorides is carried out using methods known from the literature (cf. e.g. Houben-Weyl, Methoden der Organischen Chemie, Volume E5/1).

(B) Reduction of the Nitrile Group:

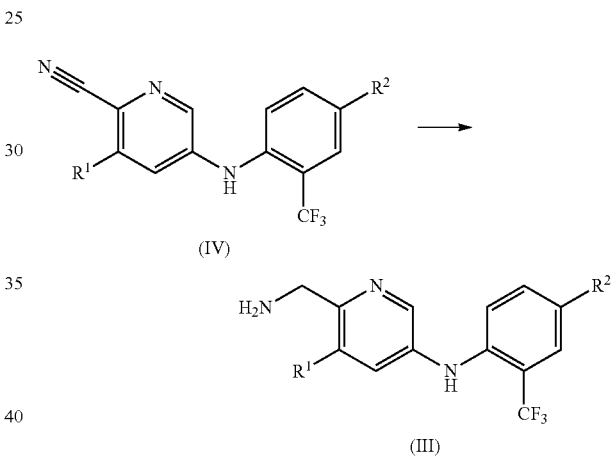

The reduction of a nitrile of general formula IV, wherein $R^1$ and $R^2$ are as hereinbefore defined, to an amine of general formula III, wherein $R^1$ and $R^2$ are as hereinbefore defined, may be carried out under standard conditions of catalytic hydrogenolysis with a catalyst, such as for example Raney nickel, in a solvent, such as for example ammoniacal methanol or ethanol, or with a reducing agent such as for example lithium aluminium hydride or sodium borohydride, in a solvent such as tetrahydrofuran, optionally in the presence of a Lewis acid such as aluminium chloride.

(C) Nucleophilic Aromatic Substitution or Transition Metal-Catalysed Coupling:

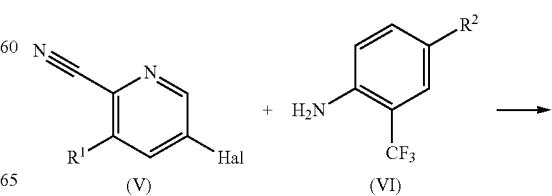

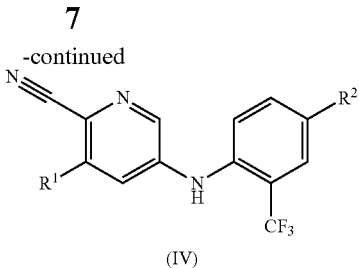

(IV)

The reaction of an aniline of general formula VI, wherein $R^2$ is as hereinbefore defined, with a nitrile of general formula V, wherein $R^1$ is as hereinbefore defined and Hal denotes a fluorine, chlorine or bromine atom, is carried out according to known methods, for example in a solvent such as tetrahydrofuran, dimethylformamide or dimethylsulphoxide and conveniently in the presence of a base, such as for example triethylamine, sodium hydroxide solution or potassium carbonate, at a temperature of 20° C. to 160° C. If the aniline of general formula VI is liquid, the reaction may also be carried out without a solvent and additional base.

An alternative method of preparing compounds of general formula IV, wherein $R^1$ and $R^2$ are as hereinbefore defined, is the palladium-catalysed reaction of a nitrile of general formula V, wherein $R^1$ is as hereinbefore defined and Hal denotes a fluorine, chlorine or bromine atom, with an aniline of general formula VI, wherein $R^2$ is as hereinbefore defined. Reaction conditions for this reaction, also known as the Buchwald-Hartwig reaction, are known from the literature.

Description of the Method of Binding the cynoBK1-Receptor

CHO cells that express the cynomolgus BK1-receptor are cultivated in "HAM'S F-12 Medium". The medium is removed from confluent cultures, the cells are washed with PBS buffer, scraped off or detached using Versene and isolated by centrifuging. Then the cells are homogenised in suspension, the homogenate is centrifuged and resuspended. After the protein content has been determined 200 µl of the homogenate (50 to 250 µg protein/assay) are incubated for 60-180 minutes at ambient temperature with 0.5 to 5.0 nM kallidin (DesArg10,Leu9), [3,4-Prolyl-3,43H(N)] and increasing concentrations of the test substance in a total volume of 250 µl. The incubation is stopped by rapid filtration through GF/B glass fibre filters that have been pre-treated with polyethyleneimine (0.3%). The radioactivity bound to the protein is measured with a TopCount NXT. The radioactivity bound in the presence of 1.0 µM kallidin (DesArg10) is defined as non-specific binding. The concentration binding curve may be analysed using computer-aided non-linear curve fitting to determine the corresponding $K_i$ values for the test substance.

Test results of the cynoBK1 receptor binding assay:

| Example No. | $K_i$ [nM] |
|---|---|
| (5) | 5.6 |

INDICATIONS

In view of their pharmacological properties, the new compounds and their physiologically acceptable salts are suitable for treating diseases and symptoms of diseases caused at least to some extent by stimulation of bradykinin-B1 receptors, or in which antagonisation of the bradykinin-B1 receptor can bring about an improvement in symptoms.

In a further aspect the present invention encompasses the compounds of the above-mentioned general formula I according to the invention for use as medicaments.

In view of their pharmacological effect the substances are suitable for the treatment of (a) acute pain such as e.g. toothache, peri- and postoperative pain, traumatic pain, muscle pain, the pain caused by burns, sunburn, trigeminal neuralgia, pain caused by colic, as well as spasms of the gastro-intestinal tract or uterus;

(b) visceral pain such as e.g. chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(c) neuropathic pain such as e.g. painful neuropathies, pain of diabetic neuropathy, AIDS-associated neuropathic pain, non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves, as well as central pain such as for example after stroke, bone marrow injuries or tumours;

(d) inflammatory/pain receptor-mediated pain in connection with diseases such as for example osteoarthritis, rheumatoid arthritis, rheumatic fever, tendo-synovitis, bursitis, tendonitis, gout and gout-arthritis, traumatic arthritides, vulvodynia, damage to and diseases of the muscles and fascia, juvenile arthritis, spondylitis, psoriasis-arthritis, myositis, dental disease, influenza and other virus infections such as colds, systemic lupus erythematodes or pain caused by burns, (e) tumour pain associated with cancers such as for example lymphatic or myeloid leukaemia, Hodgkin's disease, non-Hodgkin's lymphomas, lymphogranulomatosis, lymphosarcomas, solid malignant tumours and extensive metastases;

(f) headache diseases of various origins such as for example cluster headaches, migraine (with or without aura) and tension headaches;

(g) pain of mixed origins such as for example chronic back pain, including lumbago, or fibromyalgia.

The compounds are also suitable for treating (h) inflammatory diseases or phenomena caused by sunburn and burns, inflammation of the gums, oedema after burns trauma, cerebral oedema and angiooedema, intestinal complaints including Crohn's diseases and ulcerative colitis, irritable bowel syndrome, pancreatitis, nephritis, cystitis (interstitial cystitis), uveitis; inflammatory skin diseases (such as e.g. psoriasis and eczema), vascular diseases of the connective tissue, sprains and fractures, as well as musculoskeletal diseases with inflammatory symptoms such as acute rheumatic fever, polymyalgia rheumatica, reactive arthritides, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren's syndrome, Still's disease or Felty syndrome;

(i) inflammatory changes connected with diseases of the airways such as bronchial asthma, including allergic asthma (atopic and non-atopic) as well as bronchospasm on exertion, occupationally induced asthma, viral or bacterial exacerbation of an existing asthma and other non-allergically induced asthmatic diseases;

(j) chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round), vasomotor rhinitis and diseases caused by dust in the lungs such as aluminosis, anthracosis, asbestosis, chalicosis, siderosis, silicosis, tabacosis and byssinosis, exogenous allergic alveolitis, cystic fibrosis, bronchiectasis, pulmonary diseases in alpha1-antitrypsin deficiency and cough;

(k) diabetes mellitus and its effects (such as e.g. diabetic vasculopathy, diabetic neuropathy, diabetic retinopathy) and diabetic symptoms in insulitis (for example hyperglycaemia, diuresis, proteinuria and increased renal excretion of nitrite and kallikrein);

(l) sepsis and septic shock after bacterial infections or after trauma;

(m) syndromes that cause itching (pruritis) and allergic skin reactions;

(n) damage to the central nervous system;

(o) wounds and tissue damage;

(p) benign prostatic hyperplasia and hyperactive bladder;

(q) vascular diseases such as panarteriitis nodosa, polyarthritis nodosa, periarteriitis nodosa, arteriitis temporalis, Wegner's granulomatosis, giant cell arteriitis, arteriosclerosis and erythema nodosum;

(r) disorders of motility or spasms of respiratory, genitourinary, gastro-intestinal including biliary or vascular structures and organs;

(s) post-operative fever;

(t) for the treatment and prevention of cardiovascular diseases such as high blood pressure and related complaints;

(u) for the treatment and prevention of cancer and related complaints;

(v) for the treatment and prevention of psychiatric diseases such as depression;

(w) for the treatment and prevention of urinary incontinence and related complaints;

(x) for the treatment and prevention of morbid obesity and related complaints;

(y) for the treatment and prevention of atherosclerosis and related complaints; and (z) for the treatment and prevention of epilepsy.

The substances are suitable for causal treatment in the sense of slowing down or stopping the progress of chronically progressive diseases, particularly osteoarthritis, rheumatoid arthritis and spondylarthritis.

In another aspect the present invention encompasses the use of the compounds of the above-mentioned general formula I according to the invention for preparing a medicament for therapeutic use in the above-mentioned indications.

Preferably, the compounds of general formula I according to the invention are used for the treatment of osteoarthritis, rheumatoid arthritis or COPD.

The term "treatment" or "therapy" refers to a therapeutic treatment of patients with a manifest, acute or chronic indication, including on the one hand symptomatic (palliative) treatment to relieve the symptoms of the disease and on the other hand causal or curative treatment of the indication with the aim of ending the pathological condition, reducing the severity of the pathological condition or delaying the progression of the pathological condition, depending on the nature or gravity of the indication.

The present invention further relates to the use of a compound of general formula I for preparing a medicament for the acute and prophylactic treatment of acute pain, visceral pain, neuropathic pain, inflammatory/pain receptor-mediated pain, tumour pain, headache pain and pain of mixed causes and other diseases as mentioned above. This use is characterised in that it comprises administering an effective amount of a compound of general formula I or a physiologically acceptable salt thereof to a patient requiring such treatment.

The term "patient" preferably refers to a human being.

In addition to their suitability as therapeutic drugs for humans, these substances are also useful in the veterinary medical treatment of domestic pets, exotic animals and farmed animals.

COMBINATIONS

For treating pain, it may be advantageous to combine the compounds according to the invention with stimulants such as caffeine or other pain-relieving active compounds. If active compounds suitable for treating the cause of the pain are available, these can be combined with the compounds according to the invention.

The following compounds may be used for combination therapy, for example:

Non-steroidal antirheumatics (NSAR) such as for example propionic acid derivatives which may be selected from among alminoprofen, bucloxic acid, carprofen, fenoprofen, ibuprofen, ketoprofen, naproxen, oxaprozin, pirprofen, pranoprofen and tiaprofenic acid; acetic acid derivatives which may be selected from among indomethacin, acemetacin, alclofenac, isoxepac, sulindac and tolmetin; fenamic acid derivatives which may be selected from among meclofenamic acid, mefenamic acid and tolfenamic acid; biphenyl-carboxylic acid derivatives; oxicams which may be selected from among meloxicam, piroxicam and tenoxicam; salicylic acid derivatives which may be selected from among acetylsalicylic and sulphasalazine; pyrazolones which may be selected from among apazone and feprazone); and coxibs which may be selected from among celecoxib and etoricoxib.

Opiate receptor agonists which may for example be selected from among morphine, Darvon, tramadol and buprenorphine;

Cannabinoid agonists such as for example GW-1000;

Sodium channel blockers which may for example be selected from among carbamazepine, mexiletinee, pregabalin, tectin and ralfinamide.

N-type calcium channel blockers such as for example ziconotide.

Serotonergic and noradrenergic modulators which may be selected from among for example duloxetine and amitriptyline.

Corticosteroids which may be selected from among for example betamethasone, budesonide, cortisone, dexamethasone, hydrocortisone, methylprednisolone, prednisolone, prednisone and triamcinolone.

Histamine H1-receptor antagonists which may for example be selected from among bromopheniramine, chloropheniramine, dexchlorpheniramine, triprolidine, clemastine, diphenhydramine, diphenylpyraline, tripelennamine, hydroxyzine, promethazine, trimeprazine, azatadine, cyproheptadine, antazoline, pheniramine, pyrilamine, loratadine, cetirizine, desloratadine, fexofenadine and levocetirizine.

Leukotriene antagonists and 5-lipoxygenase inhibitors which may for example be selected from among zafirlukast, montelukast, pranlukast and zileuton.

Local anaesthetics which may for example be selected from among ambroxol and lidocaine.

TRVP1 antagonists which may for example be selected from among AZD-1386, JTS-653 and PHE-377.

Nicotine receptor agonists such as for example A-366833.

P2X3-receptor antagonists such as e.g. A-317491.

anti-NGF antibodies and NGF antagonists which may for example be selected from among JNJ-42160443 and PPH 207.

NK1 and NK2 antagonists such as e.g. CP-728663.

NMDA antagonists which may for example be selected from among CNS-5161, AZ-756 and V-3381.

Potassium channel modulators such as e.g. CL-888.

GABA modulators such as e.g. baclofen.

Anti-migraine drugs such as e.g. sumatriptan, zolmitriptan, naratriptan and eletriptan.

For treating one or more of the above-mentioned respiratory complaints it may be advantageous to combine the compounds of general formula I according to the invention with other active substances for treating respiratory complaints. If suitable active substances for treating the cause of the respiratory complaints are available, these may be combined with the compounds according to the invention.

The compounds of general formula I may optionally also be used in conjunction with other pharmacologically active substances. It is preferable to use active substances of the type selected from among the betamimetics, anticholinergics, corticosteroids, PDE-IV inhibitors, LTD4-receptor antagonists, inhibitors of MAP kinases, EGFR-inhibitors, H1-receptor antagonists, H4-receptor antagonists, PAF-antagonists, PI3-kinase inhibitors, CXCR1 and/or CXCR2 receptor antagonists and anti-tussives.

Betamimetics used according to the invention are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharine, isoprenaline, levosalbutamol, mabuterol, meluadrin, metaproterenol, milveterol, orciprenaline, pirbuterol, procaterol, reproterol, rimiterol, ritodrin, salmefamol, soterenol, sulphonterol, terbutaline, tiaramide, tolubuterol and zinterol or 6-hydroxy-8-{1-hydroxy-2-[2-(4-methoxy-phenyl)-1,1-dimethyl-ethylamino]-ethyl}-4H-benzo[1,4]oxazin-3-one, 8-{2-[2-(2,4-difluoro-phenyl)-1,1-dimethyl-ethylamino]-1-hydroxy-ethyl}-6-hydroxy-4H-benzo[1,4]oxazin-3-one, 8-{2-[2-(3,5-difluoro-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 8-{2-[2-(4-fluoro-phenyl)-1,1-dimethyl-ethylamino]-1-hydroxy-ethyl}-6-hydroxy-4H-benzo[1,4]oxazin-3-one, N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide, N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide, 8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one, 8-{2-[1,1-dimethyl-3-(3-methyl-2-oxo-2,3-dihydro-benzimidazol-1-yl)-propylamino]-1-hydroxy-ethyl}-6-hydroxy-4H-benzo[1,4]oxazin-3-one, N-[2-hydroxy-5-((1R)-1-hydroxy-2-{2-[4-(2-hydroxy-2-phenyl-ethylamino)-phenyl]-ethylamino}-ethyl)-phenyl]-formamide, 8-hydroxy-5-((1R)-1-hydroxy-2-{2-[4-(6-methoxy-biphenyl-3-ylamino)-phenyl]-ethylamino}-ethyl)-1H-quinolin-2-one, 8-hydroxy-5-[(1R)-1-hydroxy-2-(6-phenethylamino-hexylamino)-ethyl]-1H-quinolin-2-one, 5-[(1R)-2-(2-{4-[4-(2-amino-2-methyl-propoxy)-phenylamino]-phenyl}-ethylamino)-1-hydroxy-ethyl]-8-hydroxy-1H-quinolin-2-one,

[3-(4-{6-[(2R)-2-hydroxy-2-(4-hydroxy-3-hydroxymethyl-phenyl)-ethylamino]-hexyloxy}-butyl)-5-methyl-phenyl]-urea, 4-((1R)-2-{6-[2-(2,6-dichloro-benzyloxy)-ethoxy]-hexylamino}-1-hydroxy-ethyl)-2-hydroxymethyl-phenol, 3-(4-{6-[(2R)-2-hydroxy-2-(4-hydroxy-3-hydroxymethyl-phenyl)-ethylamino]-hexyloxy}-butyl)-benzenesulphonamide, 3-(3-{7-[(2R)-2-hydroxy-2-(4-hydroxy-3-hydroxymethyl-phenyl)-ethylamino]-heptyloxy}-propyl)-benzenesulphonamide, 4-((1R)-2-{6-[4-(3-cyclopentanesulphonyl-phenyl)-butoxy]-hexylamino}-1-hydroxy-ethyl)-2-hydroxymethyl-phenol, N-1-Adamantanyl-2-{3-[(2R)-2-({(2R)-2-hydroxy-2-[4-hydroxy-3-(hydroxymethyl)-phenyl]ethyl}amino)propyl]phenyl}acetamide, (1R)-5-{2-[6-(2,2-difluoro-2-phenyl-ethoxy)-hexylamino]-1-hydroxy-ethyl}-8-hydroxy-1H-quinolin-2-one (R,S)-4-(2-{[6-(2,2-difluoro-4-phenylbutoxy)hexyl]amino}-1-hydroxy-ethyl)-2-(hydroxyl-methyl)phenol, (R,S)-4-(2-{[6-(2,2-difluoro-2-phenylethoxy)hexyl]amino}-1-hydroxy-ethyl)-2-(hydroxyl-methyl)phenol, (R,S)-4-(2-{[4,4-difluoro-6-(4-phenylbutoxy)hexyl]amino}-1-hydroxy-ethyl)-2-(hydroxyl-methyl)phenol, (R,S)-4-(2-{[6-(4,4-difluoro-4-phenylbutoxy)hexyl]amino}-1-hydroxy-ethyl)-2-(hydroxyl-methyl)phenol, (R,S)-5-(2-{[6-(2,2-difluoro-2-phenylethoxy)hexyl]amino}-1-hydroxy-ethyl)-8-hydroxyquinolin-2(1H)-one, (R,S)-2-({6-[2,2-difluoro-2-(3-methylphenyl)ethoxy]hexyl}amino)-1-hydroxyethyl]-2-(hydroxymethyl)phenol, 4-(1R)-2-{[6-(2,2-difluoro-2-phenylethoxy)hexyl]amino}-1-hydroxyethyl)-2-(hydroxyl-methyl)phenol, (R,S)-2-(hydroxymethyl)-4-(1-hydroxy-2-{[4,4,5|5-tetrafluoro-6-(3-phenylpropoxy)-hexyl]amino}ethyl)phenol, (R,S)-5-(2-{[6-(2,2-difluoro-2-phenylethoxy)hexyl]amino}-1-hydroxy-ethyl)-2-hydroxy-phenyl]formamide, (R,S)-4-[2-({6-[2-(3-bromophenyl)-2,2-difluoroethoxy]hexyl}amino)-1-hydroxyethyl]-2-(hydroxymethyl)phenol, (R,S)—N-[3-(1,1-difluoro-2-{[6-({2-hydroxy-2-[4-hydroxy-3-(hydroxymethyl)phenyl]-ethyl}amino)hexyl]oxy}ethyl)phenyl]-urea, 3-[3-(1,1-difluoro-2-{[6-({2-hydroxy-2-[4-hydroxy-3-(hydroxymethyl) phenyl]ethyl}-amino)hexyl]oxy}ethyl)phenyl]imidazolidin-2,4-dione, (R,S)-4-[2-({6-[2,2-difluoro-2-(3-methoxyphenyl)ethoxy]hexyl}amino)-1-hydroxyethyl]-2-(hydroxymethyl)phenol, 5-((1R)-2-{[6-(2,2-difluoro-2-phenylethoxy)hexyl]amino}-1-hydroxyethyl)-8-hydroxyquinolin-2(1H)-one, 4-((1R)-2-{[4,4-difluoro-6-(4-phenylbutoxy)hexyl]amino}-1-hydroxy-ethyl)-2-(hydroxyl-methyl)phenol, (R,S)-4-(2-{[6-(3,3-difluoro-3-phenylpropoxy)hexyl]amino}-1-hydroxy-ethyl)-2-(hydroxylmethyl)phenol, (R,S)-(2-{[6-(2,2-difluoro-2-phenylethoxy)-4,4-difluoro-hexyl]amino}-1-hydroxyethyl)-2-(hydroxymethyl)phenol, (R,S)-4-(2-{[6-(2,2-difluoro-3-phenylpropoxy)hexyl]amino}-1-hydroxyethyl)-2-(hydroxyl-methyl)phenol, 3-[2-(3-chloro-phenyl)-ethoxy]-N-(2-diethylamino-ethyl)-N-{2-[2-(4-hydroxy-2-oxo-2,3-dihydro-benzothiazole-7-yl)-ethylamino]-ethyl}-propionamide, N-(2-diethylamino-ethyl)-N-{2-[2-(4-hydroxy-2-oxo-2,3-dihydro-benzothiazole-7-yl)-ethylamino]-ethyl}-3-(2-naphthalen-1-yl-ethoxy)-propionamide, 7-[2-(2-{3-[2-(2-chloro-phenyl)-ethylamino]-propylsulphanyl}-ethylamino)-1-hydroxy-ethyl]-4-hydroxy-3H-benzothiazol-2-one, optionally in the form of their racemates, enantiomers, diastereomers and optionally in the form of the pharmacologically acceptable acid addition salts, solvates or hydrates thereof. Preferably, according to the invention, the acid addition salts of the betamimetics are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Anticholinergics used according to the invention are preferably compounds selected from among the tiotropium salts, preferably the bromide salt, oxitropium salts, preferably the bromide salt, flutropium salts, preferably the bromide salt, Ipratropiumsalzen, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthene-9-carbonyloxy)-1-azoniabicyclo[2.2.2]octane salts. In the above-mentioned salts the cations are the pharmacologically active constituents. As anions X⁻ the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while the chloride, bromide, iodide, sulphate, methanesulphonate or p-toluenesulphonate are preferred as counter-ions. Of all the salts the chlorides, bromides, iodides and methanesulphonates are particularly preferred.

Other anticholinergics may be selected from among
tropenol 2,2-diphenylpropionate-methobromide,
scopine 2,2-diphenylpropionate-methobromide,
scopine 2-fluoro-2,2-diphenylacetate methobromide,
tropenol 2-fluoro-2,2-diphenylacetate methobromide,
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide,
tropenol 9-hydroxy-fluorene-9-carboxylate methobromide,
tropenol 9-fluoro-fluorene-9-carboxylate methobromide,
scopine 9-hydroxy-fluorene-9-carboxylate methobromide,
scopine 9-fluoro-fluorene-9-carboxylate methobromide,
tropenol 9-methyl-fluorene-9-carboxylate methobromide,
scopine 9-methyl-fluorene-9-carboxylate methobromide,
cyclopropyltropine benzilate methobromide,
cyclopropyltropine 2,2-diphenylpropionate methobromide,
cyclopropyltropine 9-hydroxy-xanthene-9-carboxylate methobromide,
cyclopropyltropine 9-methyl-fluorene-9-carboxylate methobromide,
cyclopropyltropine 9-methyl-xanthene-9-carboxylate methobromide,
cyclopropyltropine 9-hydroxy-fluorene-9-carboxylate methobromide,
cyclopropyltropine methyl 4,4'-difluorobenzilate methobromide,
tropenol 9-hydroxy-xanthene-9-carboxylate methobromide,
scopine 9-hydroxy-xanthene-9-carboxylate methobromide,
tropenol 9-methyl-xanthene-9-carboxylate methobromide,
scopine 9-methyl-xanthene-9-carboxylate methobromide,
tropenol 9-ethyl-xanthene-9-carboxylate methobromide,
tropenol 9-difluoromethyl-xanthene-9-carboxylate methobromide, and
scopine 9-hydroxymethyl-xanthene-9-carboxylate methobromide.

Corticosteroids used according to the invention are preferably compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone and tipredane orpregna-1,4-dien-3,20-dione, 6-fluoro-11-hydroxy-16,17-[(1-methylethylidene)-bis(oxy)]-21-[[4-[(nitroxy)methyl]benzoyl]oxy], (6-alpha,11-beta,16-alpha)-(9Cl) (NCX-1024)
16,17-butylidenedioxy-6,9-difluoro-11-hydroxy-17-(methylthio)androst-4-en-3-one (RPR-106541),
(S)-fluoromethyl 6,9-difluoro-17-[(2-furanylcarbonyl)oxy]-11-hydroxy-16-methyl-3-oxo-androsta-1,4-diene-17-carbothionate,
(S)-(2-oxo-tetrahydrofuran-3S-yl) 6,9-difluoro-11-hydroxy-16-methyl-3-oxo-17-propionyloxy-androsta-1,4-diene-17-carbothionate, and
cyanomethyl 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylate,
optionally in the form of their racemates, enantiomers or diastereomers and optionally in the form of the salts and derivatives thereof, the solvates and/or hydrates thereof. Every reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE-IV-inhibitors used according to the invention are preferably compounds selected from among enprofyllin, theophyllin, roflumilast, ariflo (cilomilast), tofimilast, pumafentrin, lirimilast, apremilast, arofyllin, atizoram, oglemilast and tetomilast or 5-[(N-(2,5-dichloro-3-pyridinyl)-carboxamide]-8-methoxyquinoline (D-4418),
N-(3,5-dichloro-1-oxido-4-pyridinyl)-carboxamide]-8-methoxy-2-(trifluoromethyl)-quinoline (D-4396 (Sch-351591)), N-(3,5-dichloropyrid-4-yl)-[1-(4-fluorobenzyl)-5-hydroxy-indol-3-yl]glyoxylamide (AWD-12-281 (GW-842470)), 9-[(2-fluorophenyl)methyl]-N-methyl-2-(trifluoromethyl)-9H-purin-6-amine (NCS-613), 4-[(2R)-2-[3-(cyclopentyloxy)-4-methoxyphenyl]-2-phenylethyl]-pyridine (CDP-840), N-[(3R)-3,4,6,7-tetrahydro-9-methyl-4-oxo-1-phenylpyrrolo[3,2,1-jk][1,4]benzodiazepin-3-yl]-4-pyridinecarboxamide (PD-168787), 4-[6,7-diethoxy-2,3-bis(hydroxymethyl)-1-naphthalenyl]-1-(2-methoxyethyl)-2(1H)-pyridinone (T-440), 2-[4-[6,7-diethoxy-2,3-bis(hydroxymethyl)-1-naphthalenyl]-2-pyridinyl]-4-(3-pyridinyl)-1(2H)-phthalazinone (T-2585), (3-(3-cyclopenyloxy-4-methoxybenzyl)-6-ethylamino-8-isopropyl-3H-purine (V-11294A), beta-[3-(cyclopentyloxy)-4-methoxyphenyl]-1,3-dihydro-1,3-dioxo-2H-isoindole-2-propanamide (CDC-801), imidazo[1,5-a]pyrido[3,2-e]pyrazin-6(5H)-one, 9-ethyl-2-methoxy-7-methyl-5-propyl-(D-22888)

5-[3-(cyclopentyloxy)-4-methoxyphenyl]-3-[(3-methylphenyl)methyl]-, (3S,5S)-2-piperidinone (HT-0712), 4-[1-[3,4-bis(difluoromethoxy)phenyl]-2-(3-methyl-1-oxido-4-pyridinyl)ethyl]-alpha,alpha-bis(trifluoromethyl)-benzenemethanol (L-826141), N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s]-[1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]-benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)-cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers, diastereomers and optionally in the form of the pharmacologically acceptable acid addition salts, solvates or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used according to the invention are preferably compounds selected from among montelukast, pranlukast and zafirlukast, or (E)-8-[2-[4-[4-(4-fluorophenyl)butoxy]phenyl]ethenyl]-2-(1H-tetrazol-5-yl)-4H-1-benzopyran-4-one (MEN-91507), 4-[6-acetyl-3-[3-(4-acetyl-3-hydroxy-2-propylphenylthio)propoxy]-2-propylphenoxy]-butyric acid (MN-001), 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid and

[2-[[2-(4-tert-butyl-2-thiazolyl)-5-benzofuranyl]oxymethyl]phenyl]acetic acid, optionally in the form of their racemates, enantiomers, diastereomers and optionally in the form of the pharmacologically acceptable acid addition salts, solvates or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-receptor antagonists may optionally be capable of forming are meant, for example: alkali metal salts, such as for example sodium or potassium salts, alkaline earth salts, sulphobenzoates, phosphates, isonicotinates, acetates, propionates, dihydrogen phosphates, palmitates, pivalates or furoates.

MAP Kinase inhibitors used according to the invention are preferably compounds selected from among:
Bentamapimod (AS-602801)
Doramapimod,
5-carbamoylindole (SD-169),
6-[(aminocarbonyl)(2,6-difluorophenyl)amino]-2-(2,4-difluorophenyl)-3-pyridinecarboxamide (VX-702),
alpha-[2-[[2-(3-pyridinyl)ethyl]amino]-4-pyrimidinyl]-2-benzothiazoleacetonitrile (AS-601245),
9,12-epoxy-1H-diindolo[1,2,3-fg:3',2',1'-kl]pyrrolo[3,4-i][1.6]benzodiazocine-10-carboxylic acid (CEP-1347), and
4-[3-(4-chlorophenyl)-5-(1-methyl-4-piperidinyl)-1H-pyrazol-4-yl]-pyrimidine (SC-409),
optionally in the form of their racemates, enantiomers, diastereomers and optionally in the form of the pharmacologically acceptable acid addition salts, prodrugs, solvates or hydrates thereof.

EGFR-inhibitors used according to the invention are preferably compounds selected from among cetuximab, trastuzumab, panitumumab (=ABX-EGF), Mab ICR-62, gefitinib, canertinib and erlotinib or 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline,
4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline,
4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline,
4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline,
4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline,
4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline,
4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline,
4-[(3-chloro-4-fluorophenyl)amino]-6-{[4-(N-cyclopropyl-N-methyl-amino)-1-oxo-2-buten-1-yl]amino}-7-cyclopentyloxy-quinazoline,
4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline,
4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline,
4-[(3-ethynyl-phenyl)amino]-6,7-bis-(2-methoxy-ethoxy)-quinazoline,
4-[(3-chloro-4-fluorophenyl)amino]-7-[3-(morpholin-4-yl)-propyloxy]-6-[(vinylcarbonyl)-amino]-quinazoline,
4-[(R)-(1-phenyl-ethyl)amino]-6-(4-hydroxy-phenyl)-7H-pyrrolo[2,3-d]pyrimidine,
3-cyano-4-[(3-chloro-4-fluorophenyl)amino]-6-{[4-(N,N-dimethylamino)-1-oxo-2-buten-1-yl]amino}-7-ethoxy-quinoline,
4-{[3-chloro-4-(3-fluoro-benzyloxy)-phenyl]amino}-6-(5-{[(2-methanesulphonyl-ethyl)amino]methyl}-furan-2-yl)quinazoline,
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline,
4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline,
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline,
4-[(3-ethynyl-phenyl)amino]-6-{[4-(5,5-dimethyl-2-oxo-morpholin-4-yl)-1-oxo-2-buten-1-yl]amino}-quinazoline,
4-[(3-chloro-4-fluoro-phenyl)amino]-6-[2-(2,2-dimethyl-6-oxo-morpholin-4-yl)-ethoxy]-7-methoxy-quinazoline,
4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline,
4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline,
4-[(3-chloro-4-fluoro-phenyl)amino]-6-{2-[4-(2-oxo-morpholin-4-yl)-piperidin-1-yl]-ethoxy}-7-methoxy-quinazoline,
4-[(3-chloro-4-fluoro-phenyl)amino]-6-[1-(tert-butyloxycarbonyl)-piperidin-4-yloxy]-7-methoxy-quinazoline,
4-[(3-chloro-4-fluoro-phenyl)amino]-6-(trans-4-amino-cyclohexane-1-yloxy)-7-methoxy-quinazoline,
4-[(3-chloro-4-fluoro-phenyl)amino]-6-(trans-4-methanesulphonylamino-cyclohexane-1-yloxy)-7-methoxy-quinazoline,
4-[(3-chloro-4-fluoro-phenyl)amino]-6-(tetrahydropyran-3-yloxy)-7-methoxy-quinazoline,
4-[(3-chloro-4-fluoro-phenyl)amino]-6-(1-methyl-piperidin-4-yloxy)-7-methoxy-quinazoline,
4-[(3-chloro-4-fluoro-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(methoxymethyl)carbonyl]-piperidin-4-yloxy}-7-methoxy-quinazoline,
4-[(3-chloro-4-fluoro-phenyl)amino]-6-(piperidin-3-yloxy)-7-methoxy-quinazoline,
4-[(3-chloro-4-fluoro-phenyl)amino]-6-[1-(2-acetylamino-ethyl)-piperidin-4-yloxy]-7-methoxy-quinazoline,
4-[(3-chloro-4-fluoro-phenyl)amino]-6-(tetrahydropyran-4-yloxy)-7-ethoxy-quinazoline,
4-[(3-chloro-4-fluoro-phenyl)amino]-6-((S)-tetrahydrofuran-3-yloxy)-7-hydroxy-quinazoline,
4-[(3-chloro-4-fluoro-phenyl)amino]-6-(tetrahydropyran-4-yloxy)-7-(2-methoxy-ethoxy)-quinazoline,
4-[(3-chloro-4-fluoro-phenyl)amino]-6-{trans-4-[(dimethylamino)sulphonylamino]-cyclohexane-1-yloxy}-7-methoxy-quinazoline,
4-[(3-chloro-4-fluoro-phenyl)amino]-6-{trans-4-[(morpholin-4-yl)carbonylamino]-cyclohexane-1-yloxy}-7-methoxy-quinazoline,
4-[(3-chloro-4-fluoro-phenyl)amino]-6-{trans-4-[(morpholin-4-yl)sulphonylamino]-cyclohexane-1-yloxy}-7-methoxy-quinazoline,
4-[(3-chloro-4-fluoro-phenyl)amino]-6-(tetrahydropyran-4-yloxy)-7-(2-acetylamino-ethoxy)-quinazoline,
4-[(3-chloro-4-fluoro-phenyl)amino]-6-(tetrahydropyran-4-yloxy)-7-(2-methanesulphonylamino-ethoxy)-quinazoline,
4-[(3-chloro-4-fluoro-phenyl)amino]-6-{1-[(piperidin-1-yl)carbonyl]-piperidin-4-yloxy}-7-methoxy-quinazoline,
4-[(3-chloro-4-fluoro-phenyl)amino]-6-(1-aminocarbonylmethyl-piperidin-4-yloxy)-7-methoxy-quinazoline,
4-[(3-chloro-4-fluoro-phenyl)amino]-6-(cis-4-{N-[(tetrahydropyran-4-yl)carbonyl]-N-methyl-amino}-cyclohexane-1-yloxy)-7-methoxy-quinazoline,
4-[(3-chloro-4-fluoro-phenyl)amino]-6-(cis-4-{N-[(morpholin-4-yl)carbonyl]-N-methyl-amino}-cyclohexane-1-yloxy)-7-methoxy-quinazoline,
4-[(3-chloro-4-fluoro-phenyl)amino]-6-(cis-4-{N-[(morpholin-4-yl)sulphonyl]-N-methyl-amino}-cyclohexane-1-yloxy)-7-methoxy-quinazoline,
4-[(3-chloro-4-fluoro-phenyl)amino]-6-(trans-4-ethanesulphonylamino-cyclohexane-1-yloxy)-7-methoxy-quinazoline,
4-[(3-chloro-4-fluoro-phenyl)amino]-6-(1-methanesulphonyl-piperidin-4-yloxy)-7-ethoxy-quinazoline,
4-[(3-chloro-4-fluoro-phenyl)amino]-6-(1-methanesulphonyl-piperidin-4-yloxy)-7-(2-methoxy-ethoxy)-quinazoline,
4-[(3-chloro-4-fluoro-phenyl)amino]-6-[1-(2-methoxy-acetyl)-piperidin-4-yloxy]-7-(2-methoxy-ethoxy)-quinazoline,
4-[(3-chloro-4-fluoro-phenyl)amino]-6-(cis-4-acetylamino-cyclohexane-1-yloxy)-7-methoxy-quinazoline,
4-[(3-ethynyl-phenyl)amino]-6-[1-(tert-butyloxycarbonyl-piperidin-4-yloxy)-7-methoxy-quinazoline, 4-[(3-ethynyl-phenyl)amino]-6-(tetrahydropyran-4-yloxy]-7-methoxy-quinazoline,
4-[(3-chloro-4-fluoro-phenyl)amino]-6-(cis-4-{N-[(piperidin-1-yl)carbonyl]-N-methyl-amino}-cyclohexane-1-yloxy)-7-methoxy-quinazoline,
4-[(3-chloro-4-fluoro-phenyl)amino]-6-(cis-4-{N-[(4-methyl-piperazin-1-yl)carbonyl]-N-methyl-amino}-cyclohexane-1-yloxy)-7-methoxy-quinazoline,
4-[(3-chloro-4-fluoro-phenyl)amino]-6-{cis-4-[(morpholin-4-yl)carbonylamino]-cyclohexane-1-yloxy}-7-methoxy-quinazoline,
4-[(3-chloro-4-fluoro-phenyl)amino]-6-{1-[2-(2-oxopyrrolidin-1-yl)ethyl]-piperidin-4-yloxy}-7-methoxy-quinazoline,
4-[(3-chloro-4-fluoro-phenyl)amino]-6-{1-[(morpholin-4-yl)carbonyl]-piperidin-4-yloxy}-7-(2-methoxy-ethoxy)-quinazoline,
4-[(3-ethynyl-phenyl)amino]-6-(1-acetyl-piperidin-4-yloxy)-7-methoxy-quinazoline,
4-[(3-ethynyl-phenyl)amino]-6-(1-methyl-piperidin-4-yloxy)-7-methoxy-quinazoline,
4-[(3-ethynyl-phenyl)amino]-6-(1-methanesulphonyl-piperidin-4-yloxy)-7-methoxy-quinazoline,
4-[(3-chloro-4-fluoro-phenyl)amino]-6-(1-methyl-piperidin-4-yloxy)-7(2-methoxy-ethoxy)-quinazoline,
4-[(3-chloro-4-fluoro-phenyl)amino]-6-(1-isopropyloxycarbonyl-piperidin-4-yloxy)-7-methoxy-quinazoline,
4-[(3-chloro-4-fluoro-phenyl)amino]-6-(cis-4-methylamino-cyclohexane-1-yloxy)-7-methoxy-quinazoline,
4-[(3-chloro-4-fluoro-phenyl)amino]-6-{cis-4-[N-(2-methoxy-acetyl)-N-methyl-amino]-cyclohexane-1-yloxy}-7-methoxy-quinazoline,
4-[(3-ethynyl-phenyl)amino]-6-(piperidin-4-yloxy)-7-methoxy-quinazoline,
4-[(3-ethynyl-phenyl)amino]-6-[1-(2-methoxy-acetyl)-piperidin-4-yloxy]-7-methoxy-quinazoline,
4-[(3-ethynyl-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(cis-2,6-dimethyl-morpholin-4-yl)carbonyl]-piperidin-4-yloxy}-7-methoxy-quinazoline,
4-[(3-chloro-4-fluoro-phenyl)amino]-6-{1-[(2-methyl-morpholin-4-yl)carbonyl]-piperidin-4-yloxy}-7-methoxy-quinazoline,
4-[(3-chloro-4-fluoro-phenyl)amino]-6-{1-[(S,S)-(2-oxa-5-aza-bicyclo[2.2.1]hept-5-yl)-carbonyl]-piperidin-4-yloxy}-7-methoxy-quinazoline,
4-[(3-chloro-4-fluoro-phenyl)amino]-6-{1-[(N-methyl-N-2-methoxyethyl-amino)carbonyl]-piperidin-4-yloxy}-7-methoxy-quinazoline,
4-[(3-chloro-4-fluoro-phenyl)amino]-6-(1-ethyl-piperidin-4-yloxy)-7-methoxy-quinazoline,
4-[(3-chloro-4-fluoro-phenyl)amino]-6-{1-[(2-methoxyethyl)carbonyl]-piperidin-4-yloxy}-7-methoxy-quinazoline,
4-[(3-chloro-4-fluoro-phenyl)amino]-6-{1-[(3-methoxypropyl-amino)-carbonyl]-piperidin-4-yloxy}-7-methoxy-quinazoline,
4-[(3-chloro-4-fluoro-phenyl)amino]-6-[cis-4-(N-methanesulphonyl-N-methyl-amino)-cyclohexane-1-yloxy]-7-methoxy-quinazoline,
4-[(3-chloro-4-fluoro-phenyl)amino]-6-[cis-4-(N-acetyl-N-methyl-amino)-cyclohexane-1-yloxy]-7-methoxy-quinazoline,
4-[(3-chloro-4-fluoro-phenyl)amino]-6-(trans-4-methylamino-cyclohexane-1-yloxy)-7-methoxy-quinazoline,
4-[(3-chloro-4-fluoro-phenyl)amino]-6-[trans-4-(N-methanesulphonyl-N-methyl-amino)-cyclohexane-1-yloxy]-7-methoxy-quinazoline,
4-[(3-chloro-4-fluoro-phenyl)amino]-6-(trans-4-dimethylamino-cyclohexane-1-yloxy)-7-methoxy-quinazoline,
4-[(3-chloro-4-fluoro-phenyl)amino]-6-(trans-4-{N-[(morpholin-4-yl)carbonyl]-N-methyl-amino}-cyclohexane-1-yloxy)-7-methoxy-quinazoline,
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline,
4-[(3-chloro-4-fluoro-phenyl)amino]-6-(1-methanesulphonyl-piperidin-4-yloxy)-7-methoxy-quinazoline,
4-[(3-chloro-4-fluoro-phenyl)amino]-6-(1-cyano-piperidin-4-yloxy)-7-methoxy-quinazoline,
3-cyano-4-[(3-chloro-4-fluorophenyl)amino]-6-{[4-(N,N-dimethylamino)-1-oxo-2-buten-1-yl]amino}-7-ethoxy-quinoline;
[4-[(3-chloro-4-fluorophenyl)amino]-6-{[4-(homomorpholin-4-yl)-1-oxo-2-buten-1-yl]-amino}-7-[(S)-(tetrahydrofuran-3-yl)oxy]-quinazoline,
4-[(3-chloro-4-fluorophenyl)amino]-7-(2-{4-[(S)-(2-oxotetrahydrofuran-5-yl)carbonyl]-piperazin-1-yl}-ethoxy)-6-[(vinylcarbonyl)amino]-quinazoline,
4-[(3-chloro-4-fluorophenyl)amino]-7-[2-((S)-6-methyl-2-oxo-morpholin-4-yl)-ethoxy]-6-[(vinylcarbonyl)amino]-quinazoline,
4-[(3-chloro-4-fluorophenyl)amino]-7-[4-((R)-6-methyl-2-oxo-morpholin-4-yl)-butyloxy]-6-[(vinylcarbonyl)amino]-quinazoline,
4-[(3-chloro-4-fluorophenyl)amino]-7-[4-((S)-6-methyl-2-oxo-morpholin-4-yl)-butyloxy]-6-[(vinylcarbonyl)amino]-quinazoline, and
4-[(3-chloro-4-fluorophenyl)amino]-6-[(4-{N-[2-(ethoxycarbonyl)-ethyl]-N-[(ethoxy-carbonyl)methyl]amino}-1-oxo-2-buten-1-yl)amino]-7-cyclopropylmethoxy-quinazoline,
optionally in the form of their racemates, enantiomers or diastereomers, optionally in the form of the pharmacologically acceptable acid addition salts, solvates and/or hydrates thereof. Preferably, according to the invention, acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H1 receptor antagonists used according to the invention are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, olopatadine, desloratidine and meclozine, optionally in the form of their racemates, enantiomers, diastereomers and optionally in the form of the pharmacologically acceptable acid addition salts, solvates or hydrates thereof. Preferably, according to the invention, the acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H4 receptor antagonists used according to the invention are preferably compounds which are selected from among (5-chloro-1H-indol-2-yl)-(4-methyl-1-piperazinyl)- methanone (JNJ-7777120), optionally in the form of their racemates, enantiomers, diastereomers and optionally in the form of the pharmacologically acceptable acid addition salts, solvates or hydrates thereof. Preferably, according to the invention, acid addition salts selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate are used.

Compounds which may be used as PAF-antagonists according to the invention are preferably compounds selected from among lexipafant and the compounds 4-(2-chlorophenyl)-9-methyl-2-[3(4-morpholinyl)-3-propanon-1-yl]-6H-thieno-[3,2-f]-[1,2,4]triazolo[4,3-a][1,4]diazepine and 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine, optionally in the form of the racemates, enantiomers, diastereomers and optionally in the form of the pharmacologically acceptable acid addition salts, solvates or hydrates thereof. Preferably, according to the invention, acid addition salts selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate are used.

Compounds which may be used as PI3-kinase inhibitors according to the invention are preferably compounds selected from among 5-(quinoxalin-6-ylmethylene)thiazolidine-2,4-dione (AS-605240), 2-[(6-amino-9H-purin-9-yl)methyl]-5-methyl-3-(2-methylphenyl)-4(3H)-quinazolinone (C-87114) and 2-methyl-2-[4-[3-methyl-2-oxo-8-(quinolin-3-yl)-2,3-dihydroimidazo[4,5-c]quinolin-1-yl]phenyl]propionitrile (BEZ-235), optionally in the form of the racemates, enantiomers, diastereomers and optionally in the form of the pharmacologically acceptable acid addition salts, prodrugs, solvates or hydrates thereof.

Compounds which may be used as CXCR1 or CXCR2 antagonists according to the invention are preferably compounds selected from among 3-[[3-[(dimethylamino)carbonyl]-2-hydroxyphenyl]amino]-4-[[(R)-1-(5-methylfuran-2-yl)propyl]amino]cyclobut-3-ene-1,2-dione (SCH-527123), optionally in the form of the racemates, enantiomers, diastereomers and optionally in the form of the pharmacologically acceptable acid addition salts, prodrugs, solvates or hydrates thereof.

Antitussive substances used according to the invention are preferably compounds selected from among hydrocodone, caramiphen, carbetapentane and dextramethorphane, optionally in the form of their racemates, enantiomers, diastereomers and optionally in the form of the pharmacologically acceptable acid addition salts, prodrugs, solvates or hydrates thereof.

The dosage necessary for obtaining a pain-relieving effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case one to three times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hard fat, or suitable mixtures thereof.

EXPERIMENTAL SECTION

Mass spectra and/or $^1$H-NMR spectra are generally available for the prepared compounds. The ratios specified for the eluants relate to units by volume of the respective solvents. The units by volume specified in the case of ammonia are based on a concentrated solution of ammonia in water.

Unless otherwise stated, the acid, base and salt solutions used in working up the reaction solutions are aqueous systems having the stated concentrations. For chromatographic purifications, silica gel obtained from Millipore (MATREX™, 35 to 70 µm) or Alox (E. Merck, Darmstadt, aluminium oxide 90 standardised, 63 to 200 µm, Item no. 1.01097.9050) is used.

In the test descriptions the following abbreviations are used:

TLC thin layer chromatogram
DIPEA diisopropylethylamine
DMA N,N-dimethylacetamide
DMAP 4-dimethylaminopyridine
DMF N,N-dimethylformamide
DMSO dimethylsulphoxide
HATU O-(7-azabenzotriazol-1-yl)-N,N,N',N'-tetramethyluronium hexafluorophosphate
$Pd_2(dba)_3$ tris(dibenzylideneacetone)-dipalladium(0)
RP reverse phase
$R_t$ retention time
tert tertiary
TBTU 2-(1H-benzotriazol-1-yl)-1,1,3,3-tetramethyluronium-tetrafluoroborate
TEA triethylamine
THF tetrahydrofuran
XPhos 2-dicyclohexyl-phosphino-2',4',6'-tri-isopropyl-1,1'-biphenyl The following analytical HPLC method was used:

Method 1: column: Merck Cromolith Flash RP18e, 4.6×25 mm eluant A: water/0.1% formic acid
eluant B: acetonitrile/0.1% formic acid
gradient:

| time in min | % A | % B | flow rate in mL/min |
|---|---|---|---|
| 0.0 | 90.0 | 10.0 | 1.6 |
| 2.7 | 10.0 | 90.0 | 1.6 |
| 3.0 | 10.0 | 90.0 | 1.6 |
| 3.3 | 90.0 | 10.0 | 1.6 |

Preparation of the End Compounds

Example 1

6-oxo-1,6-dihydro-pyridazine-4-carboxylic acid (3-{[5-(4-chloro-2-trifluoromethyl-phenylamino)-3-fluoro-pyridin-2-ylmethyl]-carbamoyl}-tetrahydro-furan-3-yl)-amide 1a) tert-butyl 5-bromo-3-fluoro-pyridin-2-ylmethyl)-carbamate

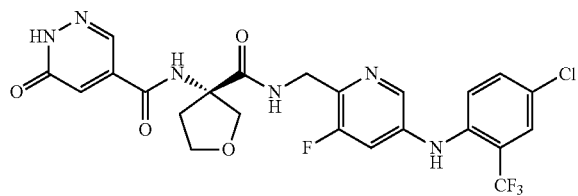 [SMILES: O=C(N[C@@]1(C(=O)NCc2ncc(Nc3ccc(Cl)cc3C(F)(F)F)cc2F)CCOC1)c1cn[nH]c(=O)c1]

A solution of 2-aminomethyl-3-fluoro-5-bromo-pyridine (185 mg, 0.77 mmol) in 8 mL of dichloromethane was combined with 0.32 mL of triethylamine and di-tert-butyl-dicarbonate (167.2 mg, 0.77 mmol) while cooling with an ice bath and then stirred overnight at ambient temperature. After standard working up of the reaction mixture the product was obtained in a yield of 72% of theory.

$C_{11}H_{14}BrFN_2O_2$ (305.14)

MS (ESI): [M+H]+=305/7

HPLC: $R_t$=2.31 min (method 1)

1b) tert-butyl [5-(4-chloro-2-trifluoromethyl-phenylamino)-3-fluoro-pyridin-2-ylmethyl]-carbamate

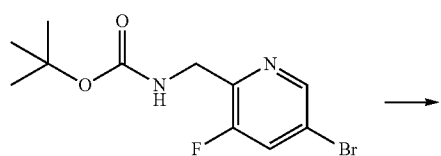

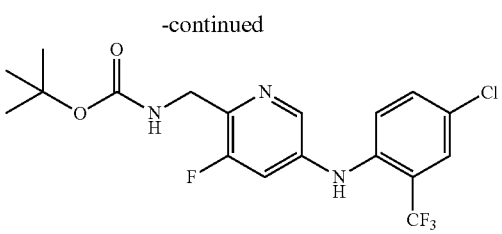

Pd$_2$(dba)$_3$ (10.8 mg) and Xphos (22.6 mg) were added under nitrogen to a solution of tert-butyl 5-bromo-3-fluoro-pyridin-2-ylmethyl)-carbamate (170 mg, 0.56 mmol), 4-chloro-2-trifluoromethyl-aniline (0.079 mL, 0.56 mmol) and K$_3$PO$_4$ (181 mg) in 3 mL toluene and then the mixture was refluxed overnight with stirring. It was then filtered and the filtrate was evaporated down. The crude product thus obtained was purified by chromatography (column: Varian Pursuit XRS C18; 10 μM; 41.4×250 mm. Gradient:

acetonitrile/water/CF$_3$COOH: 10/90/0.1→100/0/0.1).
The product was thus obtained in a yield of 21.4% of theory.

$C_{18}H_{18}ClF_4N_3O_2$ (419.8)

MS (ESI): [M+H]+=420

[M−H]−=418

HPLC: $R_t$=2.89 min (method 1)

1c) (6-aminomethyl-5-fluoro-pyridin-3-yl)-(4-chloro-2-trifluoromethyl-phenyl)-amine dihydrochloride

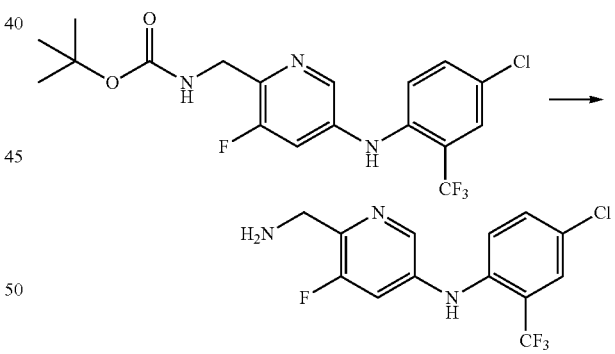

Tert-butyl [5-(4-chloro-2-trifluoromethyl-phenylamino)-3-fluoro-pyridin-2-ylmethyl]-carbamate (50 mg, 0.12 mmol) was stirred for 2 hours at 60° C. in a mixture of 2 mL of semi-concentrated hydrochloric acid and 3 mL of dioxane. This was then concentrated to dryness, the residue was stirred with 3 mL of toluene and evaporated down once more. The product was thus obtained in a yield of 84% of theory.

$C_{18}H_{18}ClF_4N_3O_2$ (319.7)

MS (ESI): [M+H]+=320/1

HPLC: $R_t$=1.73 min (method 1)

1d) n-butyl (S)-3-[(6-oxo-1,6-dihydro-pyridazine-4-carbonyl)-amino]-tetrahydrofuran-3-carboxylate

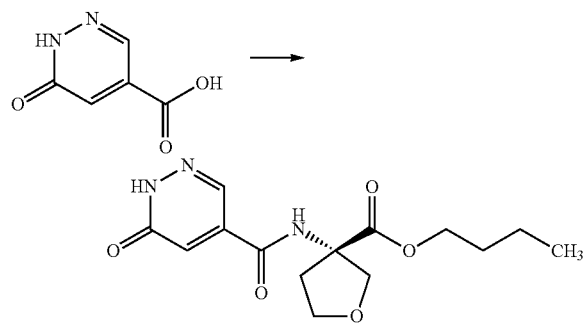

A solution of 6-oxo-1,6-dihydro-pyridazine-4-carboxylic acid (11.5 g), TBTU (25.3 g), triethylamine (20.9 mL) and 40 mL DMF in 200 mL THF was stirred for 30 minutes at ambient temperature. Then n-butyl (S)-3-amino-tetrahydrofuran-3-carboxylate (14.0 g) was added and the mixture was stirred further overnight. For working up the mixture was evaporated to dryness in vacuo and the residue was stirred with 200 mL of ethyl acetate. This solution was washed twice with 5% sodium hydrogen carbonate solution, then dried and evaporated down. The product was thus obtained in a yield of 90% of theory.

$C_{14}H_{19}N_3O_5$ (309.3)

Thin layer chromatogram (silica gel; dichloromethane/ethanol 19:1): $R_f$=0.16

1e) (S)-3-[(6-oxo-1,6-dihydro-pyridazine-4-carbonyl)-amino]-tetrahydrofuran-3-carboxylic acid

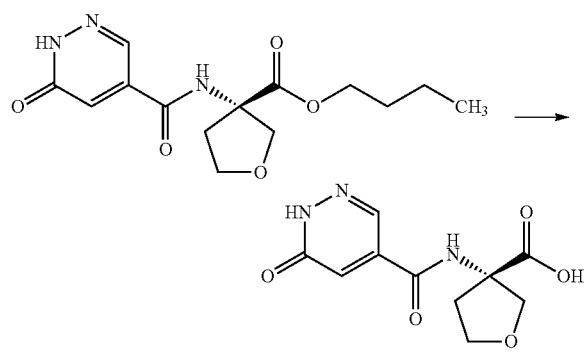

n-Butyl (S)-3-[(6-oxo-1,6-dihydro-pyridazine-4-carbonyl)-amino]-tetrahydrofuran-3-carboxylate (21.0 g) was stirred in 200 mL of 1N sodium hydroxide solution for 1 hour. The mixture was then extracted twice with 100 mL diethyl ether, and the alkaline aqueous phase was then combined with 50 mL of 4N hydrochloric acid. The mixture was then evaporated to dryness and the residue was stirred with 150 mL ethanol. Undissolved constituents were then filtered off and the filtrate was evaporated down. In this way the product was obtained in a yield of 71% of theory. The product thus obtained was further processed without any further purification.

$C_{10}H_{11}N_3O_5$ (253.2)

$^1$H-NMR ($d_6$-DMSO): δ=2.32 (m, 2H); 3.84 (t, 2H); 3.95 (d, 1H); 4.12 (d, 1H); 7.28 (s, 1H); 8.10 (s, 1H); 9.21 (broad S; 1H) ppm.

1f) (S)-6-oxo-1,6-dihydro-pyridazine-4-carboxylic acid (3-{[5-(4-chloro-2-trifluoromethyl-phenylamino)-3-fluoro-pyridin-2-ylmethyl]-carbamoyl}-tetrahydrofuran-3-yl)-amide

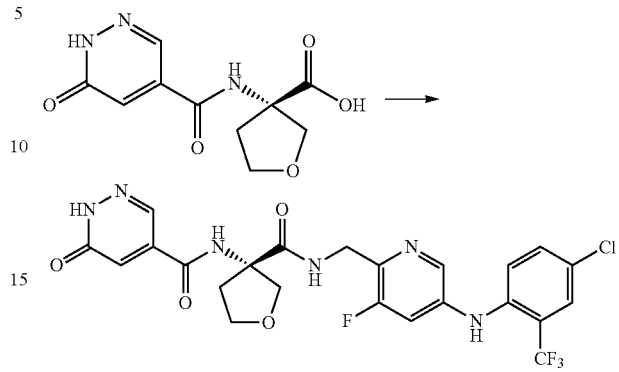

A solution of (S)-3-[(6-oxo-1,6-dihydro-pyridazine-4-carbonyl)-amino]-tetrahydrofuran-3-carboxylic acid (144.7 mg, 0.40 mmol), (6-aminomethyl-5-fluoro-pyridin-3-yl)-(4-chloro-2-trifluoromethyl-phenyl)-amine (127.9 mg, 0.40 mmol), TBTU (154 mg), triethylamine (0.112 mL) and DMF (1.0 mL) in 7 mL THF was stirred for 3 hours at ambient temperature. Then the mixture was evaporated down and the crude product thus obtained was purified by column chromatography (RP, column: YMC-Pack ODS-AQ, 5 μM).

$C_{23}H_{19}ClF_4N_6O_4$ (554.9)

MS (ESI): [M+H]+=555

[M−H]−=553

Thin layer chromatogram (silica gel; dichloromethane/methanol/ammonia 9:1:0.1): $R_f$=0.35

The following Examples describe pharmaceutical reparations which contain as active substance any desired compound of general formula I, albeit without restricting the scope of the present invention thereto:

Example I

| Dry ampoule containing 75 mg of active substance per 10 ml | |
|---|---|
| Composition: | |
| active substance | 75.0 mg |
| mannitol | 500 mg |
| water for injections | ad 10.0 ml |

Production:

Active compound and mannitol are dissolved in water. The charged ampoules are freeze dried. Water for injection is used for dissolving to give the solution ready for use.

Example II

| Tablet with 50 mg of active compound | |
|---|---|
| Composition: | |
| (1) Active compound | 50.0 mg |
| (2) Lactose | 98.0 mg |
| (3) Maize starch | 50.0 mg |

-continued

Tablet with 50 mg of active compound

Composition:

| | |
|---|---|
| (4) Polyvinylpyrrolidone | 15.0 mg |
| (5) Magnesium stearate | 2.0 mg |
| | 215.0 mg |

Production:
(1), (2) and (3) are mixed and granulated with an aqueous solution of (4). (5) is admixed to the dry granules. Tablets are compressed from this mixture, biplanar with a bevel on both sides and dividing groove on one side.
Diameter of the tablets: 9 mm.

Example III

Tablet with 350 mg of active compound

Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:
(1), (2) and (3) are mixed and granulated with an aqueous solution of (4). (5) is admixed to the dry granules. Tablets are compressed from this mixture, biplanar with a bevel on both sides and dividing groove on one side.
Diameter of the tablets: 12 mm.

Example IV

Capsules with 50 mg of active compound

Composition:

| | |
|---|---|
| (1) Active compound | 50.0 mg |
| (2) Maize starch dried | 58.0 mg |
| (3) Lactose powdered | 50.0 mg |
| (4) Magnesium stearate | 2.0 mg |
| | 160.0 mg |

Production:
(1) is triturated with (3). This triturate is added to the mixture of (2) and (4) with vigorous mixing.

This powder mixture is packed into hard gelatine size 3 two-piece capsules in a capsule-filling machine.

Example V

Capsules with 350 mg of active compound

Composition:

| | |
|---|---|
| (1) Active compound | 350.0 mg |
| (2) Maize starch dried | 46.0 mg |
| (3) Lactose powdered | 30.0 mg |
| (4) Magnesium stearate | 4.0 mg |
| | 430.0 mg |

Production:
(1) is triturated with (3). This triturate is added to the mixture of (2) and (4) with vigorous stirring.

This powder mixture is packed into hard gelatine size 0 two-piece capsules in a capsule-filling machine.

Example VI

Suppositories with 100 mg of active compound 1 suppository comprises:

| | |
|---|---|
| Active compound | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

The invention claimed is:

1. A compound of the formula I

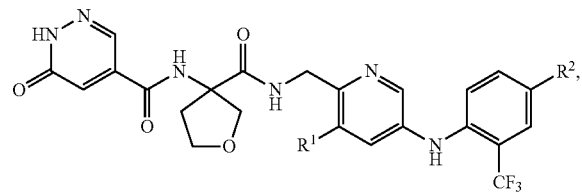

(I)

wherein
R$^1$ denotes H, Cl or F and
R$^2$ denotes Cl or F,
or a physiologically acceptable salt thereof.

2. A compound according to claim 1, selected from the group consisting of:

| No. | Structure |
|---|---|
| (1) | ![structure] |

| No. | Structure |
|---|---|
| (2) | *[structure]* |
| (3) | *[structure]* |
| (4) | *[structure]* |
| (5) | *[structure]* and |
| (6) | *[structure]* | or a physiologically acceptable salt thereof.

3. A pharmaceutical composition comprising a compound according to claim 1 together with one or more inert carriers and/or diluents.

4. A method for the treatment of osteoarthritis which comprises administering to a host suffering from the same a therapeutically effective amount of a compound according to claim 1.

* * * * *